(12) United States Patent
McAffer et al.

(10) Patent No.: US 9,908,682 B2
(45) Date of Patent: Mar. 6, 2018

(54) STORAGE OF AMPOULES CONTAINING PHARMACEUTICAL FORMULATIONS USING A SEALED CONTAINER COMPRISING AN OXYGEN SCAVENGER

(71) Applicant: Allergan Pharmaceuticals International Limited, Dublin (IE)

(72) Inventors: Ian Gardener Cameron McAffer, Tatsfield (GB); Peter Ernest Tasko, Westerham (GB)

(73) Assignee: Allergan Pharmaceuticals International Limited, Dublin (IE)

( * ) Notice: Subject to any disclaimer, the term of this patent is extended or adjusted under 35 U.S.C. 154(b) by 7 days.

(21) Appl. No.: 14/475,819

(22) Filed: Sep. 3, 2014

(65) Prior Publication Data

US 2014/0366491 A1 Dec. 18, 2014

Related U.S. Application Data

(63) Continuation of application No. 12/522,680, filed as application No. PCT/GB2008/000076 on Jan. 9, 2008, now abandoned.

(30) Foreign Application Priority Data

Jan. 9, 2007 (GB) .................................. 0700380.9

(51) Int. Cl.
*A61K 9/00* (2006.01)
*B65D 81/26* (2006.01)
(Continued)

(52) U.S. Cl.
CPC .............. *B65D 81/266* (2013.01); *A61J 1/10* (2013.01); *B65D 81/268* (2013.01); *A61J 1/067* (2013.01)

(58) Field of Classification Search
CPC . B65D 1/09; B65D 1/095; B65D 1/32; B65D 85/42; B65D 81/3277; B65D 81/3272; B65D 81/34; A61J 1/067
See application file for complete search history.

(56) References Cited

U.S. PATENT DOCUMENTS 3,826,358 A * 7/1974 Butler ................ B65D 81/1075
206/204
4,872,553 A 10/1989 Suzuki et al.
(Continued)

FOREIGN PATENT DOCUMENTS

JP 2000175989 6/2000
JP 2002065808 3/2002
(Continued)

OTHER PUBLICATIONS

Miralles, Gimenez J., International Preliminary Report on Patentability for International Application No. PCT/GB2008/000076, Apr. 2, 2009, European Patent Office, D-80298 Munich.
(Continued)

*Primary Examiner* — Anthony Stashick
*Assistant Examiner* — Robert Poon
(74) *Attorney, Agent, or Firm* — Florek & Endres PLLC

(57) ABSTRACT

Ampoules made of plastics material and containing 0.5 to 5 ml of a pharmaceutical formulation are sealed, together with an oxygen scavenger, within a pouch.

7 Claims, 1 Drawing Sheet

(51) Int. Cl.
*A61J 1/10* (2006.01)
*A61J 1/06* (2006.01)

(56) References Cited

U.S. PATENT DOCUMENTS

| | | | | |
|---|---|---|---|---|
| 5,114,003 | A * | 5/1992 | Jackisch | B65D 81/268 |
| | | | | 206/204 |
| 5,698,250 | A * | 12/1997 | Delduca | A23B 4/16 |
| | | | | 206/557 |
| 5,954,433 | A * | 9/1999 | Yeager | B65D 33/2533 |
| | | | | 383/203 |
| 6,274,169 | B1 * | 8/2001 | Abrahamson | A61K 31/593 |
| | | | | 424/400 |
| 6,688,468 | B2 * | 2/2004 | Waterman | A61J 1/00 |
| | | | | 206/524.1 |
| 6,863,865 | B2 | 3/2005 | McAffer et al. | |
| 7,413,083 | B2 * | 8/2008 | Belfance | B65D 43/162 |
| | | | | 206/204 |
| 8,771,770 | B1 * | 7/2014 | Crump | B65D 81/28 |
| | | | | 206/204 |
| 2003/0029739 | A1 * | 2/2003 | Riemenschneider | B65D 81/266 |
| | | | | 206/204 |
| 2005/0020554 | A1 | 1/2005 | Ahmed et al. | |
| 2006/0078505 | A1 | 4/2006 | McAffer et al. | |
| 2006/0177610 | A1 * | 8/2006 | McAffer | B65D 1/09 |
| | | | | 428/34.1 |
| 2007/0163917 | A1 * | 7/2007 | Friesen | A61J 1/00 |
| | | | | 206/528 |
| 2007/0207091 | A1 | 9/2007 | McAffer et al. | |
| 2008/0319006 | A1 | 12/2008 | McAffer et al. | |
| 2013/0079301 | A1 * | 3/2013 | Szabocsik | A61K 31/728 |
| | | | | 514/59 |

FOREIGN PATENT DOCUMENTS

| | | |
|---|---|---|
| WO | 03/039632 | 5/2003 |
| WO | 03/097140 | 11/2003 |
| WO | 2006/085063 | 8/2006 |
| WO | 08/062203 | 5/2008 |

OTHER PUBLICATIONS

Smith, Stephen, Search Report for Application No. GB0700380.9, The Patent Office of London, dated Mar. 16, 2007.

Database WPI, English language abstract for JP 10 287375 A, Oct. 27, 1998.

Miralles, Gimenez J., International Search Report for International Application No. PCT/GB2008/000076, dated May 16, 2008, European Patent Office, Netherlands.

* cited by examiner

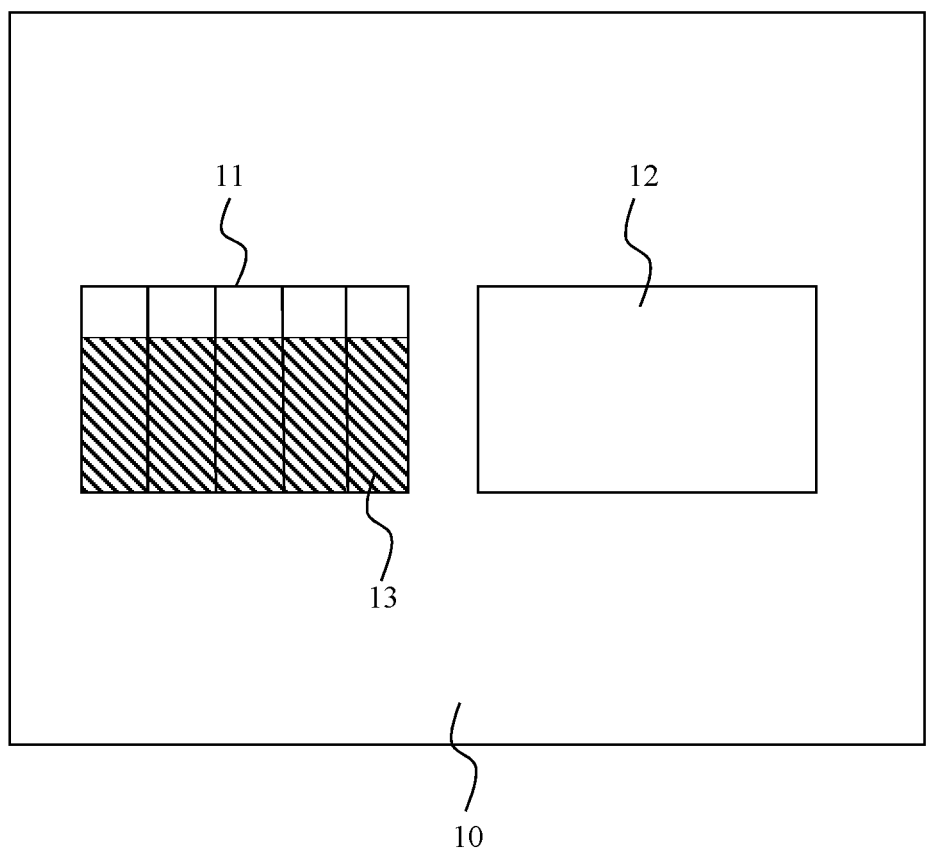

STORAGE OF AMPOULES CONTAINING PHARMACEUTICAL FORMULATIONS USING A SEALED CONTAINER COMPRISING AN OXYGEN SCAVENGER

FIELD OF THE INVENTION

The present invention relates to the sealing of containers which can be used for storage of ampoules containing pharmaceutical formulations, and in particular to sealing ampoules within a pouch to reduce or prevent oxidation of the formulations over time. The invention relates also to the sealed containers, in particular containing such ampoules.

BACKGROUND TO THE INVENTION

Pharmaceutical formulations are presented in a variety of different packaging, including packaging made of glass, metal, plastic and natural materials. For liquid formulations, e.g. solutions or suspensions, the packaging must be and remain sealed to prevent leakage. However, a number of technical and practical difficulties exist with all such containers.

It is known to administer drugs to the lungs of a patient using a nebuliser, allowing a patient to administer the drug whilst breathing normally. The drugs are provided in a unit dose ampoule (UDA), containing a relatively small volume, typically 1 mL-5 mL, of solution and typically made of plastics material. A method of making ampoules is by Blow-Fill-Seal (BFS), under aseptic conditions, in which the ampoule is formed by extrusion and filled with solution in a multi-part but essentially one-step process. If necessary, and provided the contents are not heat labile, heat sterilization can be used, e.g. ampoules can be sterilised by terminal sterilisation methods, i.e. after the ampoule has been filled and sealed. These methods are well established and accepted by regulatory authorities worldwide.

A known problem with existing ampoules is that they allow oxygen, other gases and other volatile compounds into the ampoule and allow water (moisture) to exit. Testing of the contents has revealed that, during storage, contaminants can pass through the plastic of ampoule walls and be absorbed into the formulation. As one specific example, unacceptable amounts of vanillin have been found inside ampoules, leading to failure of the product and refusal of regulatory authorities to license the ampoules without safeguards against this external contamination.

The US FDA has recently required that ampoules be over-wrapped by a sealing pouch to avoid environmental contamination of the ampoule contents. The pouch material is typically a tri-laminate of paper and/or polymer, aluminium and low density polyethylene (LDP). This pouch is regarded as an acceptable solution but the contents are still susceptible to oxidation over time. This is particularly an issue with drug formulations containing oxygen sensitive materials.

It is known to carry out the blow-fill-seal method of making and filling ampoules using nitrogen rather than sterile air during as many steps as possible in the process. Nitrogen can be used to cap the solution in the ampoule. Nitrogen can be introduced into the pouch at the time the ampoules are sealed inside the pouch. It is, however, a problem that using nitrogen in this process requires specialised equipment or modification of existing equipment. Health and safety precautions associated with the use of nitrogen tend to increase production costs and times and the efficiency of nitrogen entrapment within the pouch varies and is not totally efficient An object of the present invention is to solve or at least ameliorate the above-identified issues. An object of preferred embodiments of the invention is to provide alternative, more preferably improved methods of storing ampoules within sealed containers and to provide alternative, preferably improved sealed containers containing ampoules.

SUMMARY OF THE INVENTION

The invention is based on the use of an oxygen scavenger to reduce or prevent oxidation of formulations within ampoules sealed within containers.

In a first aspect, the invention provides a sealed container comprising (i) one or more ampoules containing up to 10 ml of a pharmaceutical formulation and (ii) an oxygen scavenger.

Preferably, the one or more ampoules are made of plastics material. Also preferably, the ampoules contain an inhalation pharmaceutical. The one or more ampoules and the oxygen scavenger are sealed within the container. In some embodiments the container material comprises a metal or metal compound, for example as a coating on or incorporated into an outside surface.

In a preferred embodiment of the invention the container is a pouch.

In a second aspect, the invention provides a method of reducing oxidative degradation of the content of an ampoule, the method comprising sealing the ampoule in a container containing an oxygen scavenger.

In a third aspect, the invention provides a method of reducing moisture egress from a container, the method comprising sealing the container in a pouch containing an oxygen scavenger.

In a fourth aspect, the invention provides a method of sealing an ampoule wherein one or more ampoules are sealed within a pouch containing an oxygen scavenger.

In a fifth aspect, the invention provides an ampoule made of plastics material, wherein the ampoule is sealed within a pouch containing an oxygen scavenger.

In a sixth aspect, the invention provides the use of an oxygen scavenger to reduce or prevent oxidation of formulations within one or more ampoules sealed within a container.

BRIEF DESCRIPTION OF THE DRAWINGS

FIG. 1 is a schematic plan view illustrating one embodiment of the sealed container of the present invention.

DETAILED DESCRIPTION OF THE INVENTION

The invention provides a package made up of one or more ampoules (11) wrapped within a container (10) (e.g. a pouch) comprising an oxygen scavenger (12). The invention also provides 5, 10, 20, 30 or more ampoules (11) sealed with the oxygen scavenger (12) within the container (10), the ampoules (11) conveniently being in a strip. Alternatively, individual ampoules or a combination of one or more strips and one or more individual ampoules may be sealed within the container. In use the presence of the oxygen scavenger (12) is found to significantly reduce the oxygen content within the container (10), reducing oxidation of the ampoule contents (13) over time and also improving the stability of the ampoule contents (13).

When a strip of ampoules is sealed within a container and the container is opened to detach one ampoule from the strip the remaining ampoules will be exposed to the air. However, this may not be a significant problem as oxidation of the contents of the ampoules only occurs after exposure to air over a relatively extended period of time compared to time in storage and the ampoules within the open container would typically all be used before significant oxidation could occur.

In one particular embodiment of the invention the container is re-sealable, allowing a single ampoule to be removed by the user. The container is then closed to again form a sealed container with the oxygen scavenger still in place. This will act to remove oxygen that entered the pouch while it was open and to "mop up" any further oxygen that may diffuse into the pouch. Accordingly, the lower oxygen content of the container results in reduced oxidation of the contents of the remaining ampoules over time.

In particularly preferred embodiments the container may comprise a pouch wherein the pouch material typically comprises a metal or metal compound and in some embodiments may comprise a tri-laminate. A typical tri-laminate composition may comprise paper and/or polymer, aluminium and low density polyethylene.

In a preferred embodiment of the invention the pouch is gas impermeable.

The ampoules typically comprise or are made of plastics material, especially polypropylene or polyethylene, low or high density or other polymer used in manufacture of ampoules or in the drinks industry, e.g. polyethylene terephthalate. Further, the ampoules typically contain a pharmaceutical agent, such an inhalation or injection drug, in combination with a pharmaceutically acceptable carrier.

In preferred embodiments of the invention ampoules are made of plastics material.

The ampoules described herein may typically have a volume of up to 10 ml, preferably 0.5 ml or more, or 1 to 5 ml. For example, the ampoules may contain 2 to 4 ml of an inhalation pharmaceutical.

In preferred embodiments the ampoules contain 1 ml or more or 2-3 ml of an inhalation pharmaceutical in a pharmaceutically acceptable carrier.

The oxygen scavenger as used in the invention is generally a commercially available packet or sachet as used and approved by the food industry. These oxygen scavengers do not contain leachables thereby avoiding contamination of the product with which they are stored.

The size of oxygen scavenger is typically in the range of 20 to 2000 cc, indicating the volume of oxygen it can absorb, preferably 20 to 1000 cc, more preferably 20 to 500 cc. In one embodiment of the invention a 50 cc packet is used. Notwithstanding this, it will be apparent to the skilled person that the size and capacity of the oxygen scavenger used can be varied depending upon the size of the container, the number of ampoules within the container, and the collective volume of the ampoules.

The following examples are provided in support of the invention. The content of the examples are for illustration only and are not intended to limit the scope of the invention in any way.

Example 1

Packages were prepared each containing one 4-ampoule card and one FreshPax D-50 oxygen scavenger packet (MultiSorb) and sealed in foil. The packages were prepared in normal atmospheric conditions and contained air when sealed.

The oxygen scavenging data was analysed at timed intervals using a Mocon Head Space Analyzer, the results of which can be seen below:

| Time | $O_2$ content within foil |
|---|---|
| 0 hours | 19.9% |
| 16 hours | 566 ppm |
| 23 hours | 435 ppm |
| 8 days | 0 ppm |
| 14 days | 0 ppm |
| 28 days | 0 ppm |
| 84 days | 0 ppm |

A control package with no oxygen scavenger measured 20.5% $O_2$ at 8 days.

Example 2

This study was designed to demonstrate the effectiveness of oxygen scavengers in preventing degradation of the product, thereby reducing the impurity levels present in the solution after storage.

The solutions for nebulisation were manufactured in 3 ml LDPE ampoules using blow-fill-seal technology. The strips of 5 were then sealed in a foil over wrap to prevent water loss from and external contamination of the product.

One batch of Levalbuterol/Ipratropium Bromide Solution for Nebulisation (1.25 mg/0.5 mg/2 ml) combination product was manufactured in 2006. Two sublots of this batch were produced and labelled Sublot 1 (ampoules were sealed in a foil pouch containing an oxygen scavenger) and Sublot 2 (ampoules were sealed in a standard foil pouch) stored for 12 months and then tested as set out below.

The related substance data summarised below is for product that has been stored for 12 months at 25° C./60% RH.

| | Batch 04906A | |
|---|---|---|
| | Sublot 1 (Oxygen Scavenger) | Sublot 2 (No Oxygen Scavenger) |
| Known impurities: | | |
| H-Tropic acid | 0.04% | 0.09% |
| Apo-Ipratropium | Below detectable levels | 0.03% |
| Bis Ether Salbutamol | 0.15% | 0.13% |
| Total known impurities | 0.19% | 0.25% |
| Largest unknown impurity | 0.11% | 0.19% |
| Total unknown impurties | 0.15% | 0.25% |
| Total Impurities | 0.34% | 0.50% |

It can be seen that the impurity levels detected in the product packaged with the oxygen scavenger were in general 25-40% lower than those observed in product packaged without the oxygen scavenger. Total impurity levels showed a 30% reduction when the oxygen scavenger was present in the pouch.

This study supports the hypothesis that oxygen scavengers placed within the foil pouch improve the stability profile of solutions for nebulisation in ampoules.

Example 3

This study was designed to demonstrate the effectiveness of oxygen scavengers in generating and maintaining an oxygen-free environment when ampoules are stored inside a foil pouch containing an oxygen scavenger.

Ampoules were manufactured using blow-fill-seal technology in normal atmospheric conditions and contained only air when sealed. Packages were prepared each containing four empty ampoules sealed within an aluminium pouch containing one FreshPax D-50 oxygen scavenger packet (MultiSorb).

The packages were prepared in normal atmospheric conditions and the oxygen content of air inside the pouches and ampoules on sealing was 20.5%. The packages were stored for 18 months and then tested as set out below. Oxygen content inside each pouch and inside two ampoules from each pouch was measured following internal protocols SAP 392.01 and SEP 156.01.

A Systech Gaspace Advance Oxygen Micro Headspace Analyser was used to measure oxygen content. The Gaspace instrument was calibrated with a certified gas containing 2.00% of oxygen and was also calibrated with ambient air. The oxygen concentration in the headspace of the pouches and the ampoules was measured using a 'Timed' method. A test time of 45 seconds was used. A self-adhesive septum was affixed to the pouch and plastic ampoule to ensure a good seal was obtained when sampling.

The oxygen headspace results are presented in the following table:

| Oxygen Concentration in Aluminium Pouches (molar % ± SD) n = 3 | Oxygen Concentration in Plastic Ampoules (molar % ± SD) n = 6 |
|---|---|
| 0.00 ± 0.00 | 4.99 ± 3.85 |

It can be seen that oxygen was completely removed from the pouches while the ampoules showed a 76% reduction in oxygen content.

In conclusion, the presence of the oxygen scavenger within the pouches appeared to draw oxygen out of the pouch and out of the headspace of the ampoule. Surprisingly, these results contrasted with the findings of previous internal studies which have shown that in pouches purged with nitrogen and not containing an oxygen scavenger there was no equilibration of oxygen concentration between the headspace of the ampoule and the interior of the pouch (data not shown). One possible explanation for the equilibration observed in the present study is that the oxygen scavenger acts as a driving force towards equilibrium between the two environments.

Total equilibrium may have been achieved between the ampoules and the pouches in this study following a longer storage period or, alternatively, by using a larger oxygen scavenger. Of course, the ampoules used in this study were completely filled with air and thus contained significantly more oxygen than ampoules filled with actives would contain. It is possible that due to their lower oxygen volume ampoules filled with actives would reach total equilibrium under the conditions of the present study.

The invention hence provides sealed containers containing ampoules and methods of obtaining the same.

The invention claimed is:

1. A method of reducing oxidative degradation of the contents of ampoules comprising the steps of:
    (a) preparing a plurality of ampoules consisting essentially of a plastics material and manufactured using a blow-fill-seal method under normal atmospheric conditions, wherein the ampoules contain a solution of an inhalation pharmaceutical in a pharmaceutically acceptable carrier,
    (b) sealing a packet or sachet comprising an oxygen scavenger and the plurality of ampoules in a resealable container under normal atmospheric conditions, wherein the resealable container is made of a material comprising a metal or metal compound and is gas impermeable;
    (c) unsealing the container under normal atmospheric conditions and removing one or more ampoules; and
    (d) resealing the container under normal atmospheric conditions while the packet or sachet comprising the oxygen scavenger and at least one ampoule remain in the container,
    wherein, in the absence of an oxygen scavenger, the plurality of ampoules and the resealable container maintain separate environments, and
    wherein a first oxygen concentration in a headspace of at least one ampoule prior to sealing in the resealable container is greater than a second oxygen concentration in the headspace of the at least one ampoule after sealing the resealable container.

2. The method of claim 1 wherein the plurality of ampoules is 10 or more ampoules.

3. The method of claim 1 wherein the oxygen scavenger can absorb 20 to 2000 cc of oxygen.

4. The method of claim 1 wherein the metal or metal compound is aluminum.

5. The method of claim 1 wherein the container is a pouch.

6. The method of claim 1 wherein the plurality of ampoules contain up to 10 mL of the solution of the inhalation pharmaceutical in the pharmaceutically acceptable carrier.

7. The method of claim 1 wherein the inhalation pharmaceutical comprises levalbuterol and ipratropium bromide.

* * * * *